United States Patent
Kubitschke et al.

(10) Patent No.: US 9,840,454 B2
(45) Date of Patent: Dec. 12, 2017

(54) METHOD FOR OBTAINING POLYOL ESTERS-ENRICHED PRODUCT STREAMS FROM THE SIDE-STREAMS IN POLYOL ESTER PRODUCTION

(71) Applicant: Oxea GmbH, Oberhausen (DE)

(72) Inventors: Jens Kubitschke, Essen (DE); Thorsten Kreickmann, Essen (DE); Jörg Arnold, Dinslaken (DE); Heinz Strutz, Moers (DE)

(73) Assignee: OXEA GMBH, Oberhausen (DE)

( * ) Notice: Subject to any disclaimer, the term of this patent is extended or adjusted under 35 U.S.C. 154(b) by 0 days.

(21) Appl. No.: 14/915,915

(22) PCT Filed: Oct. 9, 2014

(86) PCT No.: PCT/EP2014/002737
§ 371 (c)(1),
(2) Date: Mar. 2, 2016

(87) PCT Pub. No.: WO2015/062700
PCT Pub. Date: May 7, 2015

(65) Prior Publication Data
US 2016/0229789 A1    Aug. 11, 2016

(30) Foreign Application Priority Data
Nov. 2, 2013 (DE) .................... 10 2013 018 456

(51) Int. Cl.
*C07C 67/54* (2006.01)
*C07C 67/08* (2006.01)
*C07C 67/58* (2006.01)
*C07C 67/60* (2006.01)

(52) U.S. Cl.
CPC .............. *C07C 67/54* (2013.01); *C07C 67/08* (2013.01); *C07C 67/58* (2013.01); *C07C 67/60* (2013.01)

(58) Field of Classification Search
CPC combination set(s) only.
See application file for complete search history.

(56) References Cited

U.S. PATENT DOCUMENTS

| | | | |
|---|---|---|---|
| 2,628,249 A | 2/1953 | Bruno, Jr. | |
| 5,324,853 A | 6/1994 | Jones et al. | |
| 8,158,816 B2 * | 4/2012 | Frey | C07C 67/08 560/248 |
| 8,399,697 B2 | 3/2013 | Weber et al. | |
| 8,524,937 B2 | 9/2013 | Adamzik et al. | |
| 8,524,938 B2 | 9/2013 | Frey et al. | |
| 9,006,479 B2 | 4/2015 | Frey et al. | |

FOREIGN PATENT DOCUMENTS

| | | |
|---|---|---|
| DE | 102009048771 A1 | 4/2011 |
| DE | 102009048772 A1 | 4/2011 |
| DE | 102009048773 A1 | 4/2011 |
| DE | 102009048774 A1 | 4/2011 |
| DE | 102009048775 A1 | 4/2011 |

OTHER PUBLICATIONS

International Search Report dated Jan. 14, 2015.
Ullmann's Encyclopedia of Industrial Chemistry, 5th edition, 1985, pp. 305-320, vol. A1, VCH Verlagsgesellschaft, Germany.
Ullmann's Encyclopedia of Industrial Chemistry, 5th edition, 1990, pp. 438-440, vol. A15, VCH Verlagsgesellschaft, Weinheim, Germany.
Kirk-Othmer Encyclopedia of Chemical Technology, 3rd edition, 1978, pp. 778-789, vol. 1, John Wiley & Sons.
Kirk-Othmer Encyclopedia of Chemical Technology, 3rd edition, 1981, pp. 496-499, vol. 14, John Wiley & Sons.
Römpps Chemie-Lexikon, 8th edition, 1983, p. 2360, vol. 3, H-L, Franck'sche Verlagshandlung Stuttgart.
Goldsmith, Polyhydric Alcohol Esters of Fatty Acids, Chem. Rev., 1943, 257-349, 33.
International Preliminary Report on Patentability dated May 6, 2016.

* cited by examiner

*Primary Examiner* — Pancham Bakshi
*Assistant Examiner* — Mark R Luderer
(74) *Attorney, Agent, or Firm* — Michael W. Ferrell

(57) ABSTRACT

A process for obtaining product streams enriched with polyol esters from the secondary streams from polyol ester preparation, comprising
a) the reaction of polyols of the general formula (II)

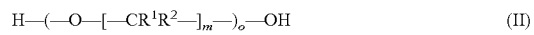

$$\text{H}-(-\text{O}-[-\text{CR}^1\text{R}^2-]_m-)_o-\text{OH} \quad \text{(II)}$$

in which $R^1$ and $R^2$ are each independently hydrogen, an alkyl radical having 1 to 5 carbon atoms or a hydroxyalkyl radical having 1 to 5 carbon atoms, m is an integer from 1 to 10, o is an integer from 2 to 15, with linear or branched aliphatic monocarboxylic acids having 3 to 20 carbon atom, with removal of the water formed;
b) the removal of unconverted starting compounds from the crude ester formed;
c) the treatment of the crude ester obtained in step b) with steam to form a volatile secondary stream; and
d) the removal of the volatile secondary stream obtained in step c),
characterized in that the volatile secondary stream obtained in step d) is separated into an aqueous phase and an organic phase and the organic phase removed is subjected to a further treatment with steam and a product stream enriched with polyol esters is obtained as residue.

20 Claims, No Drawings

METHOD FOR OBTAINING POLYOL ESTERS-ENRICHED PRODUCT STREAMS FROM THE SIDE-STREAMS IN POLYOL ESTER PRODUCTION

CLAIM FOR PRIORITY

This application is a national phase application of PCT/EP2014/002737 FILED Oct. 9, 2014 which was based on application DE 10 2013 018 456.8 FILED Nov. 2, 2013. The priorities of PCT/EP2014/002737 and DE 10 2013 018 456.8 are hereby claimed and their disclosures incorporated herein by reference.

TECHNICAL FIELD

The invention relates to a process for obtaining product streams enriched with polyol esters from the secondary streams from polyol ester preparation.

BACKGROUND

Esters of polyhydric alcohols, also called polyol esters, find a wide range of varying uses in industry, for example as plasticizers or lubricants. The selection of suitable starting materials allows the physical properties, for example boiling point or viscosity, to be controlled, and the chemical properties, such as hydrolysis resistance or stability to oxidative degradation, to be taken into account. Polyol esters can also be tailored to the solution of specific performance problems. Detailed overviews of the use of polyol esters can be found, for example, in Ullmann's Encyclopedia of Industrial Chemistry, 5th edition, 1985, VCH Verlagsgesellschaft, vol. A1, pages 305-319; 1990, vol. A15, pages 438-440, or in Kirk Othmer, Encyclopedia of Chemical Technology, 3rd edition, John Wiley & Sons, 1978, vol. 1, pages 778-787; 1981, vol. 14, pages 496-498.

The use of polyol esters as lubricants is of great industrial significance, and they are used particularly for those fields of use in which mineral oil-based lubricants only incompletely meet the requirements set. Polyol esters are used especially as turbine engine and instrument oils. Polyol esters for lubricant applications are based frequently on 1,3-propanediol, 1,3-butanediol, 1,4-butanediol, 1,2-hexanediol, 1,6-hexanediol, neopentyl glycol, trimethylolpropane, pentaerythritol, 2,2,4-trimethylpentane-1,3-diol, glycerol or 3(4),8(9)-dihydroxymethyltricyclo[5.2.1.0$^{2,6}$]decane, also known as TCD alcohol DM, as the alcohol component.

Polyol esters are also used to a considerable degree as plasticizers. Plasticizers find a variety of uses in plastics, coating materials, sealing materials and rubber articles. They interact physically with high-polymeric thermoplastic substances, without reacting chemically, preferably by virtue of their dissolution and swelling capacity. This forms a homogeneous system, the thermoplastic range of which is shifted to lower temperatures compared to the original polymers, one result being that the mechanical properties thereof are optimized, for example deformation capacity, elasticity and strength are increased, and hardness is reduced.

A specific class of polyol esters (they are referred to as G esters for short) contains diols or ether diols as the alcohol component, for example ethylene glycol, diethylene glycol, triethylene glycol, tetraethylene glycol, 1,2-propylene glycol or higher propylene glycols. They can be prepared in different ways. In addition to the reaction of alcohol and acid, optionally in the presence of acidic catalysts, further processes are employed in practice to obtain G esters, including the reaction of diol with acid halide, the transesterification of a carboxylic ester with a diol, and the addition of ethylene oxide onto carboxylic acids (ethoxylation). In industrial manufacture, only the direct reaction of diol and carboxylic acid and the ethoxylation of carboxylic acids have become established as production processes, preference usually being given to the esterification of diol and acid.

This is because this process can be performed with no particular complexity in conventional chemical apparatus, and it affords chemically homogeneous products. Compared to this, ethoxylation requires extensive and costly technical equipment.

The direct esterification of alcohols with carboxylic acids is one of the basic operations in organic chemistry. In order to increase the reaction rate, the conversion is typically performed in the presence of catalysts. The use of one of the reactants in excess and/or the removal of the water formed in the course of the reaction ensures that the equilibrium is shifted in accordance with the law of mass action to the side of the reaction product, i.e. of the ester, which means that high yields are achieved.

Comprehensive information regarding the preparation of esters of polyhydric alcohols, also including esters of ethylene glycols and fatty acids, and regarding the properties of selected representatives of these compound classes can be found in Goldsmith, Polyhydric Alcohol Esters of Fatty Acids, Chem. Rev. 33, 257 ff. (1943). For example, esters of diethylene glycol, of triethylene glycol and of polyethylene glycols are prepared at temperatures of 130 to 230° C. over reaction times of 2.5 to 8 hours. Suitable catalysts mentioned for the esterification of polyhydric alcohols are inorganic acids, acidic salts, organic sulfonic acids, acetyl chloride, metals or amphoteric metal oxides. The water of reaction is removed with the aid of an entraining agent, for example toluene or xylene, or by introducing inert gases such as carbon dioxide or nitrogen.

The production and the properties of fatty acid esters of the polyethylene glycols are discussed by Johnson (edit.), Fatty Acids in Industry (1989) Chapter 9, Polyoxyethylene Esters of Fatty Acids, and a series of preparative hints are given. Higher diester concentrations are achieved by the increase in the molar ratio of carboxylic acid to glycol. Suitable measures for removing the water of reaction are azeotropic distillation in the presence of a water-immiscible solvent, heating while passing through an inert gas, or performing the reaction under reduced pressure in the presence of a desiccant. When the addition of catalysts is dispensed with, longer reaction times and higher reaction temperatures are required. Both reaction conditions can be made milder by the use of catalysts. In addition to sulfuric acid, organic acids such as p-toluenesulfonic acid and cation exchangers of the polystyrene type are the preferred catalysts. The use of metal powders, such as tin or iron, is also described. According to the teaching from U.S. Pat. No. 2,628,249, color problems in the case of catalysis with sulfuric acid or sulfonic acid can be alleviated when working in the presence of activated carbon.

Further metallic catalysts used to prepare polyol esters are also alkoxides, carboxylates or chelates of titanium, zirconium or tin, for example according to U.S. Pat. No. 5,324, 853 A1. Such metal catalysts can be considered as high-temperature catalysts, since they achieve their full activity only at high esterification temperatures, generally above 180° C. They are frequently added not at the start of the esterification reaction, but after the reaction mixture has already been heated up and has reacted partly with elimination of water. In spite of the relatively high reaction temperatures and relatively long reaction times required compared to the conventional sulfuric acid catalysis, crude esters with a comparatively low color number are obtained in the case of catalysis with such metal compounds. Common esterification catalysts are, for example, tetraisopropyl orthotitanate, tetrabutyl orthotitanate, tetrabutyl zirconate or tin(II) 2-ethylhexanoate. Further processes for preparing polyol esters are discussed, for example, in DE 10 2009 048 771 A1, DE 10 2009 048 772 A1 and DE 10 2009 048 775 A1. In these processes, the crude ester obtained is subjected to a steam treatment in the course of workup.

It is likewise known that treatment with a peroxidic compound can be undertaken during the process of workup of the crude ester obtained after the esterification stage, in order to improve the color number of the polyol ester (DE 10 2009 048 773 A1). An analogous process using ozone or ozone-containing gases for lightening the color of polyol esters is described in DE 10 2009 048 774 A1. What is common to both processes is that the oxidative treatment is followed directly, without further intermediate steps, by a steam treatment. Advantageously, over the course of the steam treatment, excess peroxidic or ozone-containing compounds are destroyed and water introduced is removed.

However, the stream removed in the steam treatment of the crude ester contains substantial amounts of the desired polyol ester together with a number of further secondary components. In general, the stream removed in the course of steam treatment, which can also be regarded as a secondary stream, based on the organic component, contains 1%-30% by weight of monoester, 40%-80% by weight of polyol ester and, as the remainder to 100% by weight, secondary components such as starting carboxylic acid and esters thereof, low boilers and high boilers.

Since the content of polyol ester in the secondary stream removed with steam is comparatively high, there is a need for a process for recovering a product stream enriched with polyol esters from said secondary stream from polyol ester preparation and recycling it into the process for polyol ester preparation. The recovery of these additional amounts of polyol ester improves the raw material efficiency of the overall reaction and distinctly increases the capacity of the production plant with the same plant configuration without costly capital investment.

SUMMARY OF INVENTION

The invention therefore consists in a process for obtaining product streams enriched with polyol esters from the secondary streams from polyol ester preparation, comprising
a) the reaction of polyols of the general formula (II)

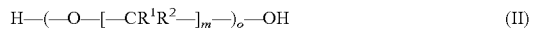

H—(—O—[—CR$^1$R$^2$—]$_m$—)$_o$—OH    (II)

in which R$^1$ and R$^2$ are each independently hydrogen, an alkyl radical having 1 to 5 carbon atoms, preferably methyl, ethyl or propyl, or a hydroxyalkyl radical having 1 to 5 carbon atoms, preferably the hydroxymethyl radical, m is an integer from 1 to 10, preferably 1 to 8 and especially 1, 2, 3 or 4, o is an integer from 2 to 15, preferably 2 to 8 and especially 2, 3, 4 or 5, with linear or branched aliphatic monocarboxylic acids having 3 to 20 carbon atoms, selected from the group of propionic acid, n-butyric acid, isobutyric acid, n-pentanoic acid, 2-methylbutyric acid, 3-methylbutyric acid, 2-methylpentanoic acid, n-hexanoic acid, 2-ethylbutyric acid, n-heptanoic acid, 2-methylhexanoic acid, 2-ethylhexanoic acid, n-nonanoic acid, 2-methyloctanoic acid, isononanoic acid, 3,5,5-trimethylhexanoic acid and 2-propylheptanoic acid, with removal of the water formed;
b) the removal of unconverted starting compounds from the crude ester formed;
c) the treatment of the crude ester obtained in step b) with steam to form a volatile secondary stream; and
d) the removal of the volatile secondary stream obtained in step c),
characterized in that the volatile secondary stream obtained in step d) is separated into an aqueous phase and an organic phase and the organic phase removed is subjected to a further treatment with steam and a product stream enriched with polyol esters is obtained as residue.

It has been found that, surprisingly, the volatile secondary stream which is obtained and removed after the treatment of the crude ester with steam can be subjected to a further steam treatment, in the course of which the content of the desired polyol ester can be concentrated.

DETAILED DESCRIPTION

The volatile secondary stream from the crude ester treatment is removed and passed into a condensation vessel in which this secondary stream is separated into an aqueous phase and an organic phase. The organic phase comprises, as well as the desired polyol ester, also the polyol and monocarboxylic acid starting compounds, monoesters and degradation products, especially in the case of esterification of ether diols. In general, the polyol ester content is 40% to 80% by weight in the organic phase removed, composed of the volatile secondary stream.

For concentration of the polyol ester content, the organic phase removed from the water-containing secondary stream is subjected again to a further steam treatment which can be effected, for example, in a simple form by introduction of steam. In the course of this, lower-boiling compounds such as the polyol or monocarboxylic acid starting compounds, and monoesters are removed. The conditions of this further steam treatment can be set in a controlled manner in order, on the one hand, to achieve sufficient removal of the volatile constituents and, on the other hand, to avoid too great a rise in the color number as a result of thermal stress. The further steam treatment is generally conducted at standard pressure, although the employment of a slightly reduced pressure, for example down to 400 hPa, is not ruled out. Operation is effected at temperatures within a range from 120 to 260° C., preferably from 150 to 220° C., until the polyol ester content is acceptable, generally over a period of 1 to 10 hours, preferably of 1 to 5 hours. Appropriately, a staged temperature profile is employed, for example commencing with the steam treatment at 120° C. and increasing the treatment temperature from stage to stage in one, two or more stages. Optionally, at the same time, the pressure can be reduced stepwise proceeding from standard pressure. The temperature and pressure conditions to be established at the particular stages, the number of stages and the respective rates of temperature increase or pressure reduction per unit time can be varied over a wide range and are guided by the requirements for the residual content of volatile components and specification values for the color number. The more intensively the steam treatment is conducted, the greater the extent to which the residual content of volatile components can be reduced, but the greater the risk of deterioration in color number. Therefore, the conditions for the further steam treatment should be set precisely, in order to achieve an acceptable compromise between the content of the desired polyol ester in the secondary stream treated and the color number.

For example, at standard pressure, starting from 150° C., the further steam treatment can first be conducted over the course of one hour, then the temperature can be pulled to 180° C. and treatment can be effected at this temperature over the course of a further hour and then, after increasing the temperature to 200° C., the steam treatment can be conducted to completion over a further period of two hours.

In one configuration of the process of the invention, the steam treatment can be conducted in the presence of an adsorbent. This involves using porous solid materials of high surface area, which are customarily used in chemical practice, both in the laboratory and in industrial plants. Examples of such materials are high-surface area polysilicic acids such as silica gels (silica xerogels), kieselguhr, high-surface area aluminas and alumina hydrates, mineral materials such as clays or carbonates, or activated carbon. Activated carbon has been found to be particularly useful. In general, the adsorbent is finely suspended in the organic phase removed, which is agitated by vigorous stirring and by introduction of steam. This achieves intimate contact between the liquid phase and the adsorbent. The amount of the adsorbent can be set substantially freely and thus in accordance with the individual requirements. Based on 100 parts by weight of the liquid phase, it has been found to be useful to use 0.1 to 5 and preferably 0.5 to 1.5 parts by weight of the adsorbent. Subsequently, the adsorbent is filtered off in conventional filtration apparatus at standard temperature or at temperatures up to 120° C., optionally in the presence of standard filtration aids such as cellulose, silica gel, kieselguhr or wood flour.

The aftertreated polyol ester is obtained as a liquid residue in the further steam treatment and generally contains product of value with a content of more than 80% by weight, preferably more than 90% by weight, based in each case on the liquid residue. Subsequently, the polyol ester thus recovered is recycled into the production process.

If necessary, the color number of the polyol ester recovered can be lowered by treatment with an oxidizing compound and immediately subsequent steam treatment, for example by treatment with an aqueous hydrogen peroxide solution as described in DE 10 2009 048 773 A1, or by treatment with ozone or ozone-containing gases by the process known from DE 10 2009 048 774 A1.

The reaction between the polyol and aliphatic monocarboxylic acid starting compounds, depending on the materials used, sets in the range from about 120 to 180° C. and can subsequently be conducted to completion in different ways.

In one configuration of the process of the invention, heating is first effected proceeding from room temperature to a temperature up to a maximum of 280° C., preferably up to 250° C., and, with the temperature kept constant, the pressure is lowered stepwise proceeding from standard pressure, in order to facilitate the removal of the water of reaction. The choice of pressure stages, whether one, two or more stages, and of the pressure to be established at the particular stage can be varied over a wide range and matched to the particular conditions. For example, in a first stage, it is possible to lower the pressure proceeding from standard pressure at first down to 600 hPa and then to conduct the reaction to completion at a pressure of 300 hPa. These pressure figures are guide values that are appropriately complied with.

As well as the variation of the pressure, it is likewise also possible to vary the temperature in one, two or more stages proceeding from room temperature during the esterification reaction, such that the temperature is increased from stage to stage with the pressure kept constant, typically up to a maximum temperature of 280° C. However, it has been found to be appropriate to heat up to a maximum of 280° C. with the temperature rising from stage to stage and also to lower the pressure from stage to stage. For example, the esterification reaction, proceeding from room temperature, can be conducted at a temperature of up to 190° C. in a first stage. A reduced pressure down to 600 hPa is likewise applied, in order to accelerate the driving-out of the water of reaction. After attainment of a temperature level of 190° C., the pressure is lowered once more to 300 hPa and the esterification reaction is conducted to completion at a temperature up to 230° C. These temperature and pressure figures are guide values that are appropriately complied with. The temperature and pressure conditions to be established in the particular stages, the number of stages and the respective rates of temperature increase or pressure reduction per unit time can be varied over a wide range and be matched according to the physical properties of the starting compounds and the reaction products, the temperature and pressure conditions of the first stage being established proceeding from standard pressure and room temperature. It has been found to be particularly appropriate to increase the temperature in two stages and lower the pressure in two stages.

The lower limit for the pressure to be established depends on the physical properties, such as boiling points and vapor pressures, of the starting compounds and the reaction products formed and is also fixed by the plant equipment. Proceeding from standard pressure, within these pressure limits, it is possible to work stepwise with pressures decreasing from stage to stage. The upper temperature limit, typically 280° C., should be complied with in order to avoid the formation of decomposition products which can have color-damaging effects inter alia. The lower limit of the temperature stages is determined by the reaction rate, which still has to be sufficiently high to complete the esterification reaction within an acceptable period. Within these limits, it is possible to work stepwise with temperatures rising from stage to stage.

The esterification can be undertaken with stoichiometric amounts of polyol and aliphatic monocarboxylic acid. Preferably, however, the polyol can be reacted with excess monocarboxylic acid, which generally has a lower boiling point than the polyol used and which can be removed by distillation in a simple manner in the subsequent workup of the crude ester. The aliphatic monocarboxylic acid is used in a 10% to 50% molar excess, preferably in a 20% to 40% molar excess, per mole of hydroxyl group to be esterified in the polyol.

The water of reaction formed is distilled out of the reaction vessel together with the excess monocarboxylic acid in the course of the esterification reaction and passed into a downstream phase separator in which monocarboxylic acid and water separate according to their solubility properties. Between the reaction vessel and phase separator may likewise be installed a fractionating column having 1 to 25, preferably 2 to 10 and especially 3 to 6 theoretical plates, in which the water-enriched fraction is passed via the top of the column into the phase separator and the monocarboxylic acid-enriched fraction flows back via the bottom of the column into the reaction vessel.

It may be the case that the monocarboxylic acid used also forms an azeotrope with water under the reaction conditions and is capable of removing the water of reaction as an entraining agent. The course of the reaction can be followed from the occurrence of water. The water separated out is removed from the process, while the monocarboxylic acid flows back into the reaction vessel from the phase separator. The addition of a further organic solvent, such as hexane, 1-hexene, cyclohexane, toluene, xylene or xylene isomer mixtures, which assumes the function of the azeotroping agent, is not ruled out but is restricted to a few exceptional cases. The azeotroping agent may be added as early as the start of the esterification reaction or after the attainment of relatively high temperatures. When the amount of water to be expected in theoretical terms has been obtained or the hydroxyl number, for example determined to DIN 53240, has fallen below a fixed value, the reaction is ended and the workup of the reaction mixture is commenced.

The reaction of polyols and aliphatic monocarboxylic acids can be conducted without using a catalyst. This variant of the reaction has the advantage of avoiding supply of extraneous substances to the reaction mixture, which can lead to unwanted contamination of the polyol ester. However, in that case, it is generally necessary to observe higher reaction temperatures, because only in this way can it be ensured that the conversion proceeds at a sufficient, i.e. economically acceptable, rate. Frequently, the aliphatic monocarboxylic acid advantageously used in excess, which is simultaneously a reaction component of the polyol, may be catalytically active, such that the esterification reaction proceeds autocatalytically.

However, the use of a catalyst which facilitates the reaction and increases the reaction rate cannot always be avoided. As well as the standard esterification catalysts such as Brønsted acids, for example sulfuric acid, methanesulfonic acid and para-toluenesulfonic acid, particularly Lewis acids containing at least one element of groups 4 to 14 of the Periodic Table of the Elements have been found to be useful, these being usable in solid or liquid form. The term "Lewis acid" in the context of the invention is understood to mean the general standard definition of such elements or compounds having an electron pair gap, as detailed, for example, in Römpp's Chemie-Lexikon, 8th edition, Franck'sche Verlagshandlung 1983, volume 3, H-L. The particularly suitable Lewis acids which can be used as catalysts in the esterification reaction include titanium, zirconium, hafnium, iron, zinc, boron, aluminum or tin, which are used as elements in finely divided form or preferably in the form of compounds. Suitable compounds are, for example, tin(II) oxide, tin(IV) oxide, tin carboxylates such as tin(II) 2-ethylhexanoate, tin(II) oxalate, tin(II) acetate or tin(IV) acetate, tin(IV) alkoxides such as tetramethyl stannate, tetraethyl stannate, tetrapropyl stannate, tetraisopropyl stannate or tetraisobutyl stannate, or organotin compounds such as butyltin maleate or dibutyltin dilaurate. The suitable titanium compounds include alkoxides such as tetramethyl orthotitanate, tetraethyl orthotitanate, tetrapropyl orthotitanate, tetraisopropyl orthotitanate, tetrabutyl orthotitanate, tetraisobutyl orthotitanate, tetrapentyl orthotitanate or tetra(2-ethylhexyl) orthotitanate; acylates such as hydroxytitanium acetate, hydroxytitanium butyrate or hydroxytitanium pentanoate; carboxylates such as titanium(IV) acetate, titanium(IV) propionate, titanium(IV) butyrate, titanium(IV) pentanoate or titanium(IV) 2-ethylhexanoate; or chelates such as tetraethylene glycol titanate or tetrapropylene glycol titanate. It is also possible to successfully use the corresponding zirconium or hafnium compounds, such as tetramethyl orthozirconate, tetraethyl orthozirconate, tetrapropyl orthozirconate, tetraisopropyl orthozirconate, tetrabutyl orthozirconate, tetraisobutyl orthozirconate, tetrapentyl orthozirconate or tetra(2-ethylhexyl) orthozirconate.

Likewise suitable are boric acid and boric esters such as trimethyl borate, triethyl borate, tripropyl borate, triisopropyl borate, tributyl borate or triisobutyl borate.

Likewise suitable are aluminum oxide, aluminum hydroxide, aluminum carboxylates such as aluminum acetate or aluminum stearate, or aluminum alkoxides such as aluminum tributoxide, aluminum tri-secbutoxide, aluminum tri-tert-butoxide or aluminum triisopropoxide.

It is also possible to use zinc oxide, zinc sulfate and zinc carboxylates such as zinc acetate dihydrate or zinc stearate, and iron(II) acetate or iron(III) hydroxide oxide, as catalysts.

The catalyst can be added to the reaction mixture as early as at the start, or only subsequently with observation of safety measures at elevated temperature, when, for example, the removal of the water of reaction has set in. The catalyst can be added in one portion or a number of portions. It is particularly advisable to add another residual amount of catalyst toward the end of the esterification reaction.

The amount of the esterification catalyst added is $1\times10^{-5}$ to 20 mol %, preferably 0.01 to 5 mol %, especially 0.01 to 2 mol %, based on the starting compound added in deficiency, appropriately based on the polyol. In the case of higher amounts of catalyst, cleavage reactions of the polyol esters are to be expected.

Particularly in the case of the preparation of polyol esters based on ether diols, for example triethylene glycol or tetraethylene glycol, in the case of use of high catalyst concentrations toward the end of the reaction and in the phase of the conversion of last residues of free hydroxyl groups, there is a risk of enhanced cleavage of the ether chain, such that the reaction temperature or the pressure to be applied should be adjusted in this case. The higher the catalyst concentration selected is, the lower the reaction temperature or the pressure to be applied should generally be selected, and an optimized temperature and pressure profile should be employed.

In one configuration of the process of the invention, the esterification can be conducted in the presence of an adsorbent. This involves using porous solid materials of high surface area, which are customarily used in chemical practice, both in the laboratory and in industrial plants. Examples of such materials are high-surface area polysilicic acids such as silica gels (silica xerogels), kieselguhr, high-surface area aluminas and alumina hydrates, mineral materials such as clays or carbonates, or activated carbon. Activated carbon has been found to be particularly useful. In general, the adsorbent is finely suspended in the reaction solution, which is agitated by vigorous stirring and by introduction of an inert gas. This achieves intimate contact between the liquid phase and the adsorbent. The amount of the adsorbent can be set substantially freely and thus in accordance with the individual requirements. Based on 100 parts by weight of the liquid reaction mixture, it has been found to be useful to use 0.1 to 5 and preferably 0.5 to 1.5 parts by weight of the adsorbent.

The reaction mixture obtained after the reaction has ended comprises, as well as the polyol ester as the desired reaction product, any unconverted starting materials, more particularly aliphatic monocarboxylic acid still in excess, when a monocarboxylic acid excess is employed according to the preferred configuration of the process of the invention. Typically, unconverted starting compounds present in excess are first distilled off, appropriately with application of a reduced pressure. If operation is effected with addition of solid esterification catalysts, for example with tin(II) oxide, zinc oxide or iron(III) hydroxide oxide, the solids are removed after the esterification reaction has ended in the course of further workup. If the esterification catalysts are added as liquid compounds, for example tetraisopropyl orthotitanate or tetrabutyl orthotitanate, which are still dissolved in the reaction mixture after the esterification reaction has ended, these compounds are converted to sparingly soluble conversion products in the course of further workup, for example by treatment with water or steam, and these can then be filtered off.

If necessary, solids and any adsorbent, if the esterification has been conducted in the presence of an adsorbent, are filtered out of the crude ester. The filtration is effected in conventional filtration apparatus at standard temperature or at temperatures up to 120° C., optionally in the presence of standard filtering aids such as cellulose, silica gel, kieselguhr or wood flour.

This is followed by a treatment with steam, which can be effected, for example, in a simple manner by introducing steam into the crude product. The steam treatment can be effected in the presence or absence of solids, according to whether a filtration step is conducted prior to the steam treatment. The steam treatment can likewise improve the color number and color stability of the crude ester.

The steam treatment is generally conducted at standard pressure, although the use of a slightly reduced pressure, appropriately down to 400 hPa, is not ruled out. The steam treatment is generally conducted at temperatures of 120 to 260° C., preferably of 150 to 220° C. and especially of 170 to 200° C., and is also guided by the physical properties of the polyol esters to be prepared in each case.

In the process step of steam treatment, it is found to be appropriate to proceed very gently during the heating period until the working temperature is attained, in order to heat the crude ester to the required temperature for the steam treatment.

The duration of the steam treatment can be determined by routine tests and is generally conducted over a period of 0.5 to 10 hours, preferably 1 to 5 hours. An excessively long steam treatment leads to an undesirable increase in the color number of the polyol ester and should therefore be avoided. An increased degradation reaction of the polyol ester to give acidic compounds is also observed, the content of which is manifested in a rise in the neutralization number or acid number, for example determined to DIN EN ISO 3682/ASTM D 1613.

Any filtration conducted may optionally be followed, immediately prior to the steam treatment of the crude esters, in order to lighten the color, by treatment with an oxidizing compound, if required by the color number of the crude ester. Suitable oxidizing compounds are peroxidic compounds or ozone and ozone-containing gases. Especially suitable is an aqueous solution of hydrogen peroxide having a hydrogen peroxide content of more than 10% by weight, preferably 30% to 50% by weight. Typically, the peroxidic compound is applied with an active content of 0.05% to 1.0% by weight, preferably of 0.08% to 0.3% by weight, based on the total amount of the crude ester to be treated. In the case of excessively high active concentrations, uncontrolled degradation reactions of the polyol esters are to be expected.

The treatment with peroxidic compounds is generally effected at temperatures of 70 to 160° C., preferably 100 to 120° C., over a treatment period of 0.5 to 3 hours. In the case of excessively long treatment times, because of the water present and the oxidizing agent, there may be increased ester cleavage and uncontrolled degradation of the polyol ester structure.

If ozone or ozone-containing gases are utilized to lighten the color, ozone is used in an amount of 0.01 to 5 grams, preferably of 0.2 to 0.8 gram, per liter of polyol ester. Higher amounts of ozone are inadvisable because of the increased onset of degradation reactions of the polyol ester skeleton. If ozone is used in a mixture with other gases, preferably in a mixture with oxygen, the ozone concentration is appropriately 2 to 200 and preferably 10 to 100 grams of ozone per $m^3$ of gas mixture. The treatment with ozone is generally effected at temperatures of 20 to 100° C., preferably 30 to 80° C., and over a period of 20 to 90 minutes.

The respective conditions for the treatment with the oxidizing compound should be tailored to the particular polyol ester, in order to achieve optimal decolorization on the one hand but to very substantially avoid degradation reactions of the polyol ester on the other hand. Especially in the case of polyol esters based on ether diols, for example triethylene glycol or tetraethylene glycol, increased degradation of the ether skeleton may set in when the conditions in the treatment with the oxidizing compound, such as temperature, contact time and active concentration, are not controlled with respect to the particular polyol ester.

After the treatment with the oxidizing reagents, the crude ester immediately thereafter, without further intermediate steps, is subjected to the treatment with steam, which can be effected, for example, in a simple form by introducing steam into the crude product. One advantage of steam treatment is that excess oxidizing compounds can be destroyed in the course thereof and residues of the starting compounds can be removed with the steam. Even relatively large amounts of water still present are driven out by the steam treatment. At the same time, this measure can improve the color number and color stability of the crude ester.

The conditions of the steam treatment that directly follows the treatment with the oxidizing reagents correspond to the aforementioned conditions for the steam treatment of the crude ester after any filtration conducted. In this context, it should be noted that, in the case of too short a treatment period, the destruction of the excess oxidizing compounds and of traces of organic peroxides formed is incomplete and the desired polyol ester still has too high an unwanted peroxide number, expressed in milliequivalents of oxygen per kilogram of product and determined to ASTM E 298. When the treatment period is too short, it is also the case that only a small advantageous effect on the color number of the polyol ester is observed.

As is the case in the treatment with the oxidizing compounds, it is also the case in the immediately subsequent steam treatment that the conditions such as temperature, pressure and duration should be controlled with respect to the particular polyol ester, in order to achieve an optimal result in relation to the color number of the polyol ester and in order to minimize residual contents of starting compounds, water and traces of peroxide, and simultaneously to suppress degradation reactions. Especially in the case of polyol esters based on ether diols, for example triethylene glycol or tetraethylene glycol, the conditions in the steam treatment should be exactly tailored to the particular polyol ester in order to prevent the unwanted degradation of the ether chain.

The residue obtained is a polyol ester of lighter color, which is subsequently dried, for example by passing an inert gas through the product at elevated temperature. Steam can also additionally be introduced in order to support the drying operation. It is also possible to simultaneously apply a reduced pressure at elevated temperature and, if necessary, to pass an inert gas through the product. Even without the action of an inert gas, it is possible to work at elevated temperature only or at relatively low pressure only. The particular drying conditions, such as temperature, pressure and duration, can be determined by simple preliminary tests. Operation is generally effected at temperatures in the range from 80 to 250° C., preferably 100 to 180° C., and at pressures of 0.2 to 500 hPa, preferably 1 to 200 hPa and especially 1 to 20 hPa. The drying, optionally together with the introduction of steam, removes residues of starting compounds, for example monocarboxylic acid, and water. The cleaned polyol ester remains as a residue in the reaction vessel during the drying. Light-colored polyol esters are obtained, which also satisfy the other specification values such as water content, residual acid content, residual monoester content and catalyst constituents, if the esterification has been catalyzed.

The volatile secondary stream from the steam treatment is removed and condensed. The condensate separates into an aqueous phase and an organic phase. Subsequently, the organic phase having a polyol ester content of generally 40% to 80% by weight, for concentration, is subjected to a further steam treatment as described above. A concentrated residue having a polyol ester content of generally more than 80% by weight, preferably more than 90% by weight, based in each case on the liquid residue, is obtained and recycled into the production process for polyol ester preparation. The amount of polyol ester additionally recovered from the volatile secondary stream can increase the capacity of the production plant and the raw material efficiency without additional capital expenditure.

Suitable polyols are compounds of the general formula (II)

$$H-(-O-[-CR^1R^2-]_m-)_o-OH \qquad (II)$$

in which $R^1$ and $R^2$ are each independently hydrogen, an alkyl radical having 1 to 5 carbon atoms, preferably methyl, ethyl or propyl, or a hydroxyalkyl radical having 1 to 5 carbon atoms, preferably the hydroxymethyl radical, m is an integer of 1 to 10, preferably 1 to 8 and especially 1, 2, 3 or 4, o is an integer of 2 to 15, preferably 2 to 8 and especially 2, 3, 4 or 5.

Suitable polyols which can be converted to light-colored polyol esters by the process of the invention are, for example, ditrimethylolpropane or dipentaerythritol.

Useful further polyols include the oligomers of ethylene glycol and 1,2-propylene glycol, especially the ether diols di-, tri- and tetraethylene glycol or dipropylene glycol, tripropylene glycol or tetrapropylene glycol. Ethylene glycols and propylene glycols are industrially produced chemicals. The base substance for preparation thereof is ethylene oxide and propylene oxide, from which 1,2-ethylene glycol and 1,2-propylene glycol are obtained by heating with water under pressure. Diethylene glycol is obtained by ethoxylation from ethylene glycol. Triethylene glycol is obtained, like tetraethylene glycol, as a by-product in the hydrolysis of ethylene oxide to prepare ethylene glycol. Both compounds can also be synthesized by reacting ethylene glycol with ethylene oxide. Dipropylene glycol, tripropylene glycol, tetrapropylene glycol and higher propoxylation products are obtainable from the multiple addition of propylene oxide onto 1,2-propylene glycol.

To obtain light-colored polyol esters in the process of the invention, linear or branched, aliphatic monocarboxylic acids having 3 to 20 carbon atoms in the molecule are used, selected from the group of propionic acid, n-butyric acid, isobutyric acid, n-pentanoic acid, 2-methylbutyric acid, 3-methylbutyric acid, 2-methylpentanoic acid, n-hexanoic acid, 2-ethylbutyric acid, n-heptanoic acid, 2-methylhexanoic acid, cyclohexanecarboxylic acid, 2-ethylhexanoic acid, n-nonanoic acid, 2-methyloctanoic acid, isononanoic acid, 3,5,5-trimethylhexanoic acid, 2-propylheptanoic acid, 2-methylundecanoic acid, isoundecanecarboxylic acid, tricyclodecanecarboxylic acid and isotridecanecarboxylic acid. The novel process has been found to be particularly useful for the preparation of polyol esters of the oligomeric ethylene glycols and of the oligomeric propylene glycols with $C_4$- to $C_{13}$- or $C_5$- to $C_{10}$-monocarboxylic acids, and for preparation of polyol esters based on ditrimethylolpropane.

The polyol esters of ethylene glycol and the oligomers thereof are outstandingly suitable as plasticizers for all common high-polymeric thermoplastic substances. They have been found to be particularly useful as an additive to polyvinyl butyral which is used admixed with glycol esters as an intermediate layer for production of multilayer or composite glasses. They can likewise be used as coalescence agents or film-forming assistants in aqueous dispersions of polymers which find various uses as coating materials. By the preparation process of the invention, it is possible in a simple manner to increase the yield of polyol esters which also satisfy the requisite quality demands, such as low odor, a low color number, a low acid number and low catalyst impurities. The process of the invention is particularly suitable for preparation of triethylene glycol di-2-ethylhexanoate (3G8 ester), tetraethylene glycol di-n-heptanoate (4G7 ester), triethylene glycol di-2-ethylbutyrate (3G6 ester), triethylene glycol di-n-heptanoate (3G7 ester) or tetraethylene glycol di-2-ethylhexanoate (4G8 ester).

The process of the invention can be performed continuously or batchwise in the reaction apparatus typical for chemical technology. Useful apparatus has been found to be stirred tanks, including in the form of a stirred tank cascade, or reaction tubes, preference being given to the batchwise reaction regime.

The examples which follow illustrate the process of the invention in detail.

WORKING EXAMPLES

For the experiments for recovery of triethylene glycol di-2-ethylhexanoate from the secondary streams, crude triethylene glycol di-2-ethylhexanoate was used, which had been obtained by esterification of triethylene glycol with a 2.4 molar amount of 2-ethylhexanoic acid with addition of 0.025 mol % of tetraisopropyl orthotitanate as catalyst, based on the triethylene glycol used, and of 0.4% by weight of activated carbon, based on the reaction mixture.

For workup of the crude triethylene glycol di-2-ethylhexanoate, the excess 2-ethylhexanoic acid was distilled off, the titanium catalyst was converted to sparingly soluble conversion products by means of steam distillation, and solids were filtered out of the crude ester. After addition of a 30% aqueous hydrogen peroxide solution in an amount of 0.1% by weight of hydrogen peroxide, absolute, the mixture was stirred at 120° C. for one hour. The subsequent steam distillation was effected over a period of one hour at a temperature of 200° C. under standard pressure.

Example 1

The volatile steam distillate obtained after the hydrogen peroxide treatment was condensed and the organic phase which separated out was separated from the aqueous phase. The organic phase separated off or the secondary stream was subjected to a further steam treatment according to the examples. The contents of triethylene glycol di-2-ethylhexanoate determined by gas chromatography (in % by weight) and the conditions for the further steam treatment are collated in table 1 below.

TABLE 1

Steam treatment of the aqueous volatile steam distillate (secondary stream) obtained in the preparation of triethylene glycol di-2-ethylhexanoate (3G8 ester)

|  | 3G8 ester content (% by weight) | Color number (according to Hazen, DIN ISO 6271) |
|---|---|---|
| Starting material | 77.5 | 14 |
| 1 h at 150° C. | 82.7 | 20 |
| 4 h at 150° C. | 86.8 | 27 |
| 1 h at 190° C. | 85.4 | 28 |
| 2 h at 190° C. | 88.8 | 49 |
| 3 h at 190° C. | 91.0 | 87 |
| 4 h at 190° C. | 92.4 | 101 |
| 1 h at 150° C., 1 h at 180° C., 2 h at 200° C. | 92.4 | 69 |

The figures in table 1 show a strong temperature dependence of the triethylene glycol di-2-ethylhexanoate content. In order to remove the low-boiling components very rapidly, higher temperatures are more effective. However, the color number likewise rises significantly at higher temperatures. If an adapted temperature profile is run, it is possible to achieve a high content of triethylene glycol di-2-ethylhexanoate and a lower color number.

Example 2

The achievable triethylene glycol di-2-ethylhexanoate content and the period of time needed therefor depend greatly on the composition of the secondary stream. Starting from a lower triethylene glycol di-2-ethylhexanoate content in the secondary stream compared to example 1, the polyol ester content achievable with the same temperature and period of time is likewise lower. In order to achieve an acceptable polyol ester content and an acceptable color number, the treatment with steam has to be adjusted in terms of temperature and duration. By means of a subsequent treatment with a 30% by weight hydrogen peroxide solution in an amount of 0.1% by weight absolute, based on the amount of polyol ester, over a period of one hour and at a temperature of 120° C., correspondingly to the process known from DE 10 2009 048773 A1, it is possible to distinctly reduce the color number.

TABLE 2

Dependence of the achievable triethylene glycol di-2-ethylhexanoate content (3G8 ester content, determined by gas chromatography) on the composition of the secondary stream and aftertreatment with hydrogen peroxide (30% aqueous solution, 1% by weight absolute based on polyol ester, one hour; 120° C.)

|  | 3G8 ester content (% by weight) | Color number* | Color number* after $H_2O_2$ treatment |
|---|---|---|---|
| Starting material | 62.1 | 14 |  |
| 4 h at 190° C. | 83.0 | 136 | 54 |
| 2 h at 150° C., 2 h at 190° C. | 80.9 | 86 | 19 |
| 1 h at 150° C., 1 h at 180° C., 2 h at 210° C. | 86.7 | 175 | 55 |
| 1 h at 150° C., 1 h at 170° C., 1 h at 190° C., 1 h at 210° C. | 84.8 | 228 | 50 |

*according to Hazen DIN ISO 6271

The invention claimed is:

1. A process for obtaining product streams enriched with polyol esters from the secondary streams from polyol ester preparation, comprising
   a) the reaction of polyols of the general formula (II)

$$H-(-O-[-CR^1R^2-]_m-)_o-OH \quad (II)$$

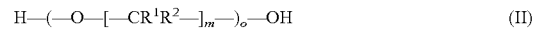

in which $R^1$ and $R^2$ are each independently hydrogen, an alkyl radical having 1 to 5 carbon atoms or a hydroxyalkyl radical having 1 to 5 carbon atoms, m is an integer from 1 to 10, o is an integer from 2 to 15, with linear or branched aliphatic monocarboxylic acids having 3 to 20 carbon atoms, selected from the group of propionic acid, n-butyric acid, isobutyric acid, n-pentanoic acid, 2-methylbutyric acid, 3-methylbutyric acid, 2-methylpentanoic acid, n-hexanoic acid, 2-ethylbutyric acid, n-heptanoic acid, 2-methylhexanoic acid, 2-ethylhexanoic acid, n-nonanoic acid, 2-methyloctanoic acid, isononanoic acid, 3,5,5-trimethylhexanoic acid and 2-propylheptanoic acid, with removal of the water formed;
   b) the removal of unconverted starting compounds from the crude ester formed;
   c) the treatment of the crude ester obtained in step b) with steam to form a volatile secondary stream; and
   d) the removal of the volatile secondary stream obtained in step c), characterized in that the volatile secondary stream obtained in step d) is separated into an aqueous phase and an organic phase and the organic phase removed is subjected to a further treatment with steam and a product stream enriched with polyol esters is obtained as residue.

2. The process as claimed in claim 1, characterized in that the further treatment with steam is conducted at a temperature of 120 to 260° C. over a period of 1 to 10 hours.

3. The process as claimed in claim 1, characterized in that the further steam treatment is conducted in a plurality of stages with temperatures rising stepwise in subsequent stages.

4. The process as claimed in claim 1, characterized in that the further steam treatment is conducted in the presence of an adsorbent.

5. The process as claimed in claim 1, characterized in that the further steam treatment is followed by a treatment with hydrogen peroxide, followed by an additional steam treatment, without any intermediate steps between the treatment with hydrogen peroxide and the additional steam treatment.

6. The process as claimed in claim 1, characterized in that the crude ester is treated with oxidizing compounds and treated in step c) without any intermediate steps beween the treatment of the crdude ester with oxidizing compounds and step c).

7. The process as claimed in claim 6, characterized in that the oxidizing compounds used are peroxidic compounds, ozone or ozone-containing gases.

8. The process as claimed in claim 7, characterized in that the peroxidic compound used is hydrogen peroxide.

9. The process as claimed in claim 1, characterized in that the polyols are reacted with the monocarboxylic acids in step a) in the presence of a catalyst.

10. The process as claimed in claim 9, characterized in that the catalyst used is titanium, zirconium, hafnium, iron, zinc, boron, aluminum or tin as elements or in the form of their compounds.

11. The process as claimed in claim 1, characterized in that the polyols are reacted with the monocarboxylic acids in step a) in the presence of an adsorbent.

12. The process as claimed in claim 11, characterized in that the adsorbent used is silica gel, kieselguhr, alumina, alumina hydrates, clays, carbonates or activated carbon.

13. The process as claimed in claim 1, characterized in that the polyols used are ditrimethylolpropane, dipentaerythritol, diethylene glycol, triethylene glycol, tetraethylene glycol, dipropylene glycol, tripropylene glycol or tetrapropylene glycol.

14. The process as claimed in claim 1 for preparing triethylene glycol di-2-ethyl-hexanoate, tetraethylene glycol di-n-heptanoate, triethylene glycol di-2-ethylbutyrate, triethylene glycol di-n-heptanoate or tetraethylene glycol di-2-ethylhexanoate.

15. The process as claimed in claim 1, in which $R^1$ and $R^2$ are each independently hydrogen, an alkyl radical selected from: methyl; ethyl or propyl; or a hydroxyalkyl radical having 1 to 5 carbon atoms, m is an integer from 1 to 10, and o is an integer from 2 to 15.

16. The process as claimed in claim 1, in which $R^1$ and $R^2$ are each independently hydrogen, an alkyl radical having 1 to 5 carbon atoms or a hydroxymethyl radical, m is an integer from 1 to 10, and o is an integer from 2 to 15.

17. The process as claimed in claim 1, in which $R^1$ and $R^2$ are each independently hydrogen, an alkyl radical having 1 to 5 carbon atoms or a hydroxyalkyl radical having 1 to 5 carbon atoms, m is an integer from 1 to 8, and o is an integer from 2 to 15.

18. The process as claimed in claim 1, in which $R^1$ and $R^2$ are each independently hydrogen, an alkyl radical having 1 to 5 carbon atoms or a hydroxyalkyl radical having 1 to 5 carbon atoms, m is 1, 2, 3 or 4, and o is an integer from 2 to 15.

19. The process as claimed in claim 1, in which $R^1$ and $R^2$ are each independently hydrogen, an alkyl radical having 1 to 5 carbon atoms or a hydroxyalkyl radical having 1 to 5 carbon atoms, m is an integer from 1 to 10, and o is an integer from 2 to 8.

20. The process as claimed in claim 1, in which $R^1$ and $R^2$ are each independently hydrogen, an alkyl radical having 1 to 5 carbon atoms or a hydroxyalkyl radical having 1 to 5 carbon atoms, m is an integer from 1 to 10, and o is 2, 3, 4, or 5.

* * * * *

UNITED STATES PATENT AND TRADEMARK OFFICE
CERTIFICATE OF CORRECTION

PATENT NO. : 9,840,454 B2
APPLICATION NO. : 14/915915
DATED : December 12, 2017
INVENTOR(S) : Jens Kubitschke et al.

Page 1 of 1

It is certified that error appears in the above-identified patent and that said Letters Patent is hereby corrected as shown below:

In the Claims

Column 15, Line 3 In Claim 5, delete "." at the end of the Claim and place a --.-- directly next to the last word in the Claim;
Column 15, Line 6 In Claim 6, delete "beween" and insert --between--; and
Column 15, Line 7 In Claim 6, delete "crdude" and insert --crude--.

Signed and Sealed this
Thirteenth Day of February, 2018

Andrei Iancu
*Director of the United States Patent and Trademark Office*